United States Patent
Kim et al.

(10) Patent No.: US 11,065,281 B2
(45) Date of Patent: Jul. 20, 2021

(54) COMPOSITION FOR PREVENTING OR TREATING ISCHEMIC ENTERITIS CONTAINING DNA FRAGMENT MIXTURE ISOLATED FROM SPERM OR TESTIS OF FISH

(71) Applicant: PharmaResearch Co., Ltd., Gangneung-si (KR)

(72) Inventors: Ik Soo Kim, Seongnam-si (KR); Seung Gul Baek, Seongnam-si (KR); Chang Ju Kim, Seoul (KR); Jung Won Jeon, Seoul (KR)

(73) Assignee: PharmaResearch Co., Ltd., Gangneung-si (KR)

( * ) Notice: Subject to any disclaimer, the term of this patent is extended or adjusted under 35 U.S.C. 154(b) by 630 days.

(21) Appl. No.: 15/739,646

(22) PCT Filed: May 25, 2016

(86) PCT No.: PCT/KR2016/005528
§ 371 (c)(1),
(2) Date: Dec. 22, 2017

(87) PCT Pub. No.: WO2016/208880
PCT Pub. Date: Dec. 29, 2016

(65) Prior Publication Data
US 2018/0185418 A1 Jul. 5, 2018
US 2019/0022148 A9 Jan. 24, 2019

(30) Foreign Application Priority Data
Jun. 26, 2015 (KR) .................. 10-2015-0090851
May 3, 2016 (KR) .................. 10-2016-0054666

(51) Int. Cl.
*A61K 35/60* (2006.01)
*A61K 47/02* (2006.01)
*A61K 9/08* (2006.01)
*A61K 9/00* (2006.01)
*A61P 1/00* (2006.01)
*A61K 31/711* (2006.01)

(52) U.S. Cl.
CPC ............ *A61K 35/60* (2013.01); *A61K 9/0019* (2013.01); *A61K 9/08* (2013.01); *A61K 31/711* (2013.01); *A61K 47/02* (2013.01); *A61P 1/00* (2018.01)

(58) Field of Classification Search
None
See application file for complete search history.

(56) References Cited

U.S. PATENT DOCUMENTS

| | | |
|---|---|---|
| 5,801,198 A | 9/1998 | Stanko et al. |
| 6,147,056 A | 11/2000 | Gilchrest et al. |
| 2009/0214630 A1 | 8/2009 | Strober et al. |
| 2011/0318365 A1 | 12/2011 | Li |
| 2014/0199402 A1 | 7/2014 | Schmidt et al. |

FOREIGN PATENT DOCUMENTS

| | | |
|---|---|---|
| JP | H05-009121 A | 1/1993 |
| JP | H11-509206 A | 8/1999 |
| JP | 2004-196701 A | 7/2004 |
| KR | 2003-0001370 A | 1/2003 |
| KR | 10-0818752 B1 | 4/2008 |
| KR | 2013-0044195 A | 5/2013 |
| KR | 10-2014-0058445 A | 5/2014 |
| WO | 00-53210 A1 | 9/2000 |
| WO | 2017/085670 A1 | 5/2017 |

OTHER PUBLICATIONS

KR20130044195A (English translation from Espacenet, https://worldwide.espacenet.com/publicationDetails/biblio?DB=EPODOC&II=0&ND=3&adjacent=true&locale=en_EP&FT=D&date=20130502&CC=KR&NR=20130044195A&KC=A) (Year: 2013).*
Hui, et al., Biologicals, 41:190. (Year: 2013).*
International Search Report issued for International Application No. PCT/KR2016/005528 dated Aug. 30, 2016 (4 pages).
Search Report Issued for European Patent Application No. 16814593.6 dated Jan. 21, 2019 (8 pages).
Malone Tessy D et al., "Retrospective review of ischemic colitis (IC) in gastroenterology (GI) and internal medicine (IM) practices over a 5-year period", Gastroenterology, vol. 120, No. 5 Supplement 1, Apr. 2001 (Apr. 2001), pp. A. 233-A.234.
Japanese Office Action Issued for Japanese Patent Application No. 2017-565766 dated Oct. 2, 2018, with English translation (6 pages).

* cited by examiner

*Primary Examiner* — Michael Barker
(74) *Attorney, Agent, or Firm* — Rothwell, Figg, Ernst & Manbeck, P.C.

(57) ABSTRACT

The present invention relates to a composition for preventing or treating ischemic enteritis containing a DNA fragment mixture isolated from sperm or testis of fish. The composition of the present invention was verified to have excellent effects in the prevention or treatment of ischemic enteritis. In addition, the composition for preventing or treating ischemic enteritis of the present invention was verified to be safe and have few side effects even when administered for a long period of time. Therefore, a medicine for ischemic enteritis, which is safe without side effects and has an excellent treatment effect, is developed by using the composition for preventing or treating ischemic enteritis of the present invention, and thus the composition of the present invention is expected to be a great help in the treatment of ischemic enteritis.

6 Claims, 3 Drawing Sheets

COMPOSITION FOR PREVENTING OR TREATING ISCHEMIC ENTERITIS CONTAINING DNA FRAGMENT MIXTURE ISOLATED FROM SPERM OR TESTIS OF FISH

CROSS-REFERENCE TO RELATED APPLICATION(S)

This application is a 35 U.S.C. 371 National Phase Entry Application from PCT/KR2016/005528, filed May 25, 2016, which claims the benefit of Korean Patent Application No. 10-2015-0090851 filed on Jun. 26, 2015; and Korean Patent Application No. 10-2016-0054666 filed on May 3, 2016, the disclosures of which are herein incorporated by reference in their entirety.

TECHNICAL FIELD

The present invention relates to a composition for preventing or treating ischemic colitis, the composition containing a DNA fragment mixture isolated from sperm or testis of fish.

BACKGROUND ART

Patients with digestive system diseases are on the rise due to various types of stress and environmental factors resulting from the development of the industrial society. Ischemia is a common disease frequently occurring in the digestive system, and refers to a state in which the supply of blood to body organs, tissues, or sites is reduced due to the contraction or occlusion of blood vessels. The reperfusion of blood occurs after ischemia and causes various after effects such as nerve cell damage. Ischemia ultimately results in irreversible damage, i.e., necrosis of cells and tissues, and a disease such as ischemic colitis may occur.

Ischemic colitis (IC) is the most common form of vascular disease invading the colon, and accounts for approximately 50-60% of all cases of ischemic gastrointestinal disease (Suh D. C. et al., 2007). Moderate ischemic colitis is characterized by nonspecific symptoms, such as abdominal pain and diarrhea, which are often improved before patients visit a hospital, and most patients with main symptoms, such as hemorrhagic diarrhea and abdominal pain, visit a hospital, but such symptoms are often improved by conservative therapy.

The most causes of ischemic colitis are difficult to identify, but ischemic colitis occurs mainly in the elderly when the mesenteric artery is occluded by thrombosis or an embolism or when the splanchnic artery is contracted by myocardial infarction or heart failure. Ischemic colitis may be caused by mesenteric venous thrombosis, drugs causing blood hyper-coagulation or hypotension, or vasculitis (Reinus J. F. et al., 1981; Hunter G. C. et al., 1988). Ischemic colitis is mainly classified into three types in view of pathology. The first is the transient reversible type in which ischemia occurs only in mucosa and submucosa and recovery is possible through conservative treatment alone; the second is the chronic type in which ischemia occurs in inner circular muscles; and the third is the fulminant type in which acute ischemia occurs in the anterior layer (Toursarkissian B et al., 1997; Bower T. C., 1993; Deana D. G. et al., 1995). About half of ischemic colitis cases are a transient reversible type which can be spontaneously cured, so only conservative therapy is sufficient. However, the other half may reach necrosis of the enteric full-layer or intestinal perforation, and in these cases, aggressive therapy including the consideration of surgery is needed due to a high mortality rate (Green B. T. et al., 2005; Jung S. H. et al., 2008).

The present inventors, while having been advancing studies using a DNA fragment mixture extracted from sperm or testis of fish, confirmed that the DNA fragment mixture inhibits cell necrosis in ischemic colitis rat models, and therefore completed the present invention.

Korean Patent Registration No. 0818752 as a prior art discloses a composition containing, as an active ingredient, siRNA inhibiting human FAF1 protein for treating ischemic disease, but does not disclose a DNA fragment mixture. Korean Patent Publication No. 2003-0001370 discloses that splanchnic ischemia can be treated using a peptide having EGF activity and a growth hormone secretion promoting hexapeptide, but is different from the present invention with respect to the DNA fragment mixture.

DETAILED DESCRIPTION OF THE INVENTION

Technical Problem

An aspect of the present invention is to provide a composition for preventing or treating ischemic colitis, the composition containing a DNA fragment mixture isolated from sperm or testis of fish.

Technical Solution

In accordance with an aspect of the present invention, there is provided a composition containing a DNA fragment mixture for preventing or treating ischemic colitis.

The DNA fragment mixture may be isolated from sperm or testis of fish.

The fish may be Salmonidae fish.

The DNA fragment mixture may have a molecular weight of 30-2,500 kDa.

Hereinafter, the present invention will be described in detail.

The DNA fragment mixture refers to a DNA molecule corresponding to a biological polymer composed of phosphate, four types of bases, and deoxyribose, wherein the DNA fragment mixture is present in a form in which fragments with a specific molecular weight are mixed.

The fish may be Salmonidae fish, preferably salmon or trout, and most preferably salmon.

The DNA fragment mixture may have a molecular weight of 30-2,500 kDa, preferably 40-2,000 kDa, and most preferably 50-1,500 kDa.

In addition, the present invention provides a pharmaceutical composition for preventing or treating ischemic colitis, the composition containing a DNA fragment mixture and a pharmaceutical excipient. The DNA fragment mixture may be added in a content of preferably 0.001-50 wt %, more preferably, 0.001-40 wt %, and most preferably, 0.001-30 wt %, relative to the total weight of the entire composition.

The pharmaceutical composition may be formulated into an oral dosage form, an external applicable dosage form, a suppository dosage form, and a sterile injection solution dosage form, such as a powder, a granule, a tablet, a capsule, a suspension, an emulsion, syrup, and an aerosol, by using conventional methods, respectively. Examples of a carrier, an excipient, and a diluent that may be contained in the pharmaceutical composition may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. A preparation is formulated by using a diluent or an excipient, such as a filler, an extender, a binder, a wetting agent, a disintegrant, or a surfactant, which is conventionally used.

The composition containing a DNA fragment mixture for preventing or treating ischemic colitis according to the present invention is preferably administered orally or through an injection.

Examples of a solid preparation for oral administration include a tablet, a pill, a powder, a granule, a capsule, and the like, and these solid preparations are formulated by mixing the extract or compound of the present invention with at least one excipient, for example, starch, calcium carbonate, sucrose, lactose, or gelatin. Also, in addition to a simple excipient, a lubricant, such as magnesium stearate or talc, may be used. Examples of a liquid preparation for oral administration may include a suspension, a liquid for an internal use, an emulsion, a syrup, and the like. In addition to commonly used simple diluents, such as water and liquid paraffin, various excipients, such as a wetting agent, a sweetener, a flavoring agent, a preservative, and the like may be contained in the liquid preparation.

An injection may be formulated in a dosage form of a sterile injection solution by a conventional method. Preferably, the composition of the present invention may be used as a sterile injection solution by being dissolved in water for injection (Korean Pharmacopoeia).

The dosage of the composition for treatment of the present invention may vary according to the age, sex, body weight of the subject to be treated, the pathological condition, the severity of the pathological condition, the administration route, and the judgment of the prescriber.

The DNA fragment mixture may be administered in a concentration of 2-25 mg/kg—preferably 2-16 mg/kg. If the dose concentration is less than 2 mg/kg, treatment effects are difficult to obtain, and if the dose concentration exceeds 25 mg/kg, the increase in treatment effect relative to the dosage is not large.

The DNA fragment mixture may be administered once a day or divided into multiple doses.

The composition for treatment of the present invention may be administered to mammals, such as mouse, livestock, and human, through various routes to prevent or treat ischemic colitis. All modes of administration may be expected, for example, oral, rectal, intravenous, muscular, subcutaneous, intrauterine dural, or intracerebral injection.

Advantageous Effects

The present invention relates to a composition for preventing or treating ischemic colitis, the composition containing a DNA fragment mixture isolated from sperm or testis of fish, and the composition of the present invention was confirmed to have an excellent prevention or treatment effect on ischemic colitis. In addition, the composition for preventing or treating ischemic colitis of the present invention was confirmed to be safe and have few side effects even during long-term administration.

Therefore, the composition for preventing or treating ischemic colitis of the present invention is used to develop medicines for ischemic colitis, which are safe and have no side effects and have excellent treatment effects. As a result, the composition is expected to be helpful in treating ischemic colitis.

In each of the drawings, (A) a normal group without ischemic colitis induction, (B) an ischemic colitis-induced group, (C) a DNA fragment mixture administration (2 mg/kg) group, (D) a DNA fragment mixture administration (4 mg/kg) group, (E) a DNA fragment mixture administration (8 mg/kg) group, and (F) a DNA fragment mixture administration (16 mg/kg) group

BEST MODE FOR CARRYING OUT THE INVENTION

Hereinafter, preferable embodiments of the present invention will be described in detail. However, the present invention is not limited to the embodiments described herein but may be embodied in other forms. Rather, the embodiments disclosed herein are provided so that these disclosures will be thorough and complete, and those skilled in the art will fully understand the concept of the present invention.

Example 1: Preparation of Animals 7 weeks old white male Sprague Dawley (S/D) rats weighing 180±5 g were used.

All rats were given free access to solid feed and water, maintained at 22-24° C. with a humidity of 60%, and housed in a laboratory environment with 12-hour day and night cycles. The rats were divided into experimental groups shown in table 1 below, and ten rats were used per experimental group.

TABLE 1

| | Ischemic colitis induction | DNA fragment mixture administration (mg/kg) |
|---|---|---|
| A | X | 0 |
| B | ○ | 0 |
| C | ○ | 2 |
| D | ○ | 4 |
| E | ○ | 8 |
| F | ○ | 16 |

Example 2: Establishment of Ischemic Colitis Animal Models

The rats reared in example 1 were anesthetized by intraperitoneal injection of Zoletil 50®. The abdomen of the anesthetized rats was open by abdominal midline incision, and then the peripheral vessels in the 4 cm-range from the descending colon were ligated. After the operation, the rats were subjected to incision suture, followed by disinfection with 1% iodine solution, and then the rats were recovered in a constant temperature and humidity device.

Example 3: Drug Administration

The ischemic colitis animal models in example 2 were administered with the DNA fragment mixture of the present invention to investigate the treatment effect thereof on ischemic colitis.

The DNA fragment mixture (molecular weight: 50-1500 kDa) was administered from 48 hours after ischemic colitis-induced surgery. The DNA fragment mixture was intraperitoneally injected at concentrations of 2, 4, 8, and 16 mg/kg with 500 µl each once a day for a total of 21 days. Here, as control groups, a normal group without ischemic colitis induction and a DNA fragment mixture non-administration ischemic colitis model group were used.

Example 4: Measurement of Temperature of the Affected Part

On the basis of the fact that heat increases in an affected part, the ischemic colitis induction was investigated using a laser thermometer (MT6, Raytek Co., CA. US) a total of four times including once before ischemic colitis induction and three times on a weekly basis after ischemic colitis induction. The results are shown in FIG. 1.

Figure 1:
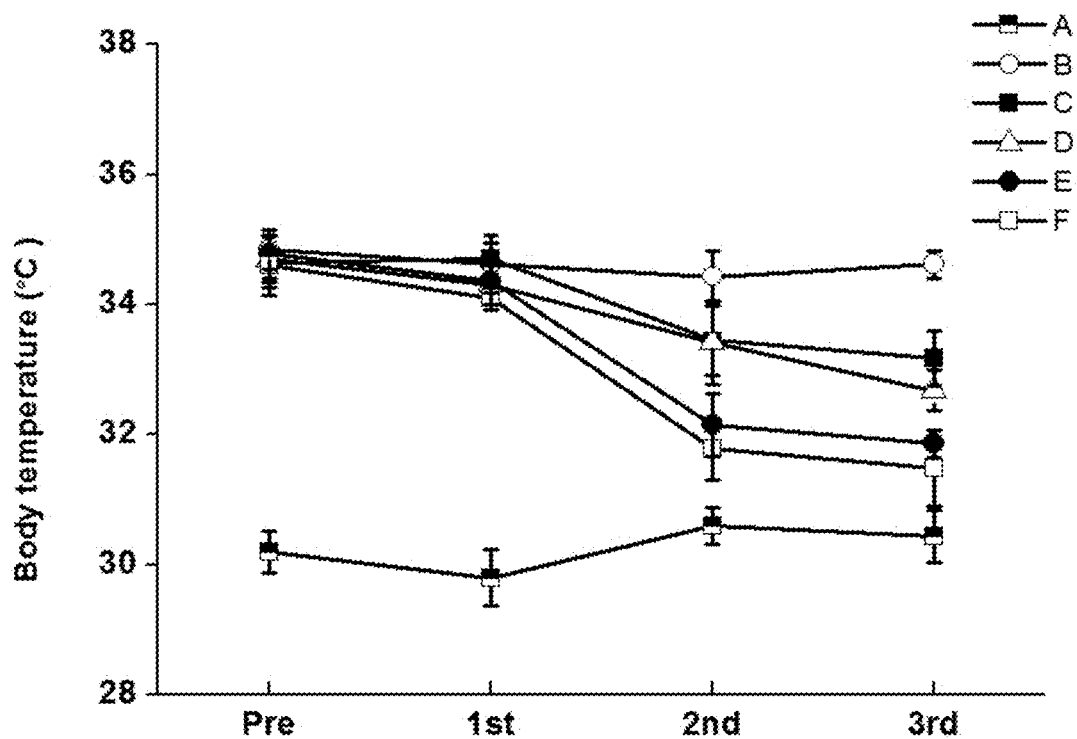
FIG. 1 shows the change of the temperature of the affected part (body temperature) caused by the occurrence of ischemic colitis.

Referring to FIG. 1, the temperature of the affected part (body temperature) after ischemic colitis induction increased in all the experimental groups excluding the normal group (A), and at the second check, the temperature of the affected part was reduced in a manner dependent on the concentration of the DNA fragment mixture. Especially, the DNA fragment mixture (16 mg/kg) administration group (F) showed the largest reduction effect. It was confirmed that the reduction in the temperature of the affected part in the DNA fragment mixture administration groups was also statistically significant at the measurement three weeks after administration of the DNA fragment mixture.

Example 5: Enteroscopy

Each rat was anesthetized by intraperitoneal injection of 10 mg/kg of Zoletil 50® 21 days after administration of the DNA fragment mixture, and then the abdomen was opened to expose the ischemic colitis-induced enteric tissue, which was then photographed at the same angle and distance. The results are shown in FIG. 2.

Figure 2:
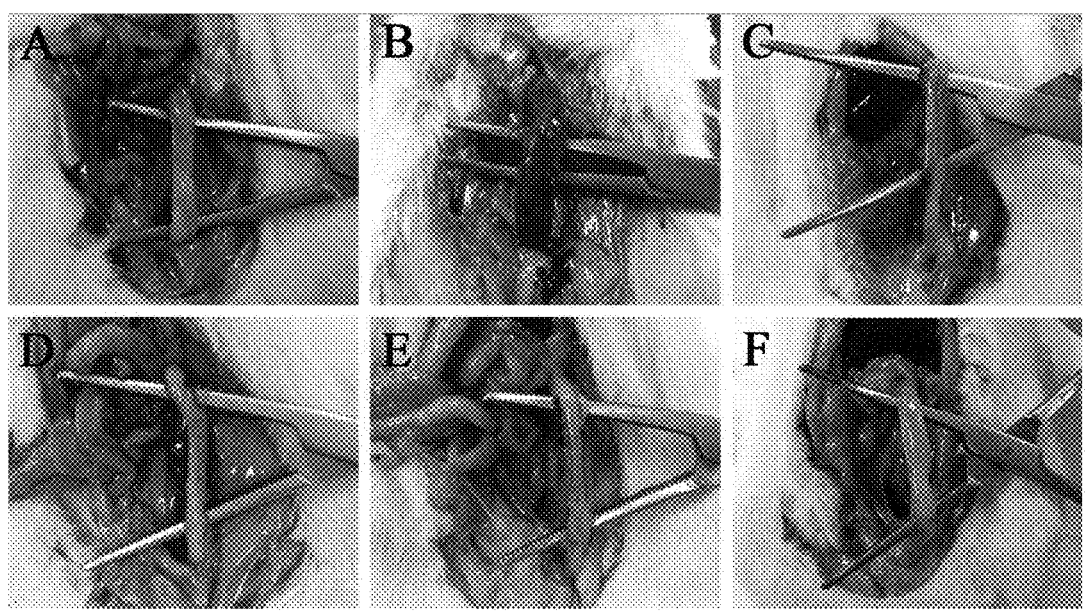
FIG. 2 shows the results of naked eye observation of the colonic tissue due to the administration of a DNA fragment mixture in ischemic colitis-induced rats.

As shown in FIG. 2, in the ischemic colitis-induced group (B), the necrosis of the colon part was increased and bleeding was observed outside the colon. Whereas in the DNA fragment mixture administration groups (C, D, E, and F), the necrosis due to ischemia was alleviated and thus the colon morphology similar to that of the normal group (A) was maintained.

It can be seen from these results that the administration of the DNA fragment mixture can inhibit or treat the ischemic colitis-induced necrosis of the colon part.

Example 6: Histological Staining

Example 6-1: Tissue Treatment

Tissues were extracted from each rat photographed for colonic tissue in example 5. Of these, some tissues were fixed for 24 hours in a 4% paraformaldehyde fixative dissolved in 100 mM phosphate buffer. Thereafter, the tissues were infiltrated with paraffin through a three-step procedure of dehydration through sequential introduction into 70%, 80%, 90%, and 100% ethanol, immersion in xylene, and then using a liquid for hard paraffin (Leica, USA). The tissue after infiltration was made into blocks in order to prepare sections, and the paraffin tissue was cut into 5 µm thick sections using a paraffin microtome (Shandon Finesse 325, Thermo Electron Co., England). The tissue section was attached on a coating slide, and left in a 37° C. slide oven for 16-18 hours.

Example 6-2: Hematoxylin and Eosin (H&E) Staining

The tissue section prepared in example 6-1 was reacted with Mayer's hematoxyline (Sigma, USA) for 30 seconds, and then washed with flowing water for 10 minutes. Thereafter, the tissue section was reacted with eosin (Sigma, USA) solution for 3 seconds. The tissue on the completion of staining was dehydrated and sealed with Permount® (Fischer Scientific, USA). The H&E stained tissue section was observed using a microscope to check the tissue change, and the results are shown in FIG. 3.

Figure 3:
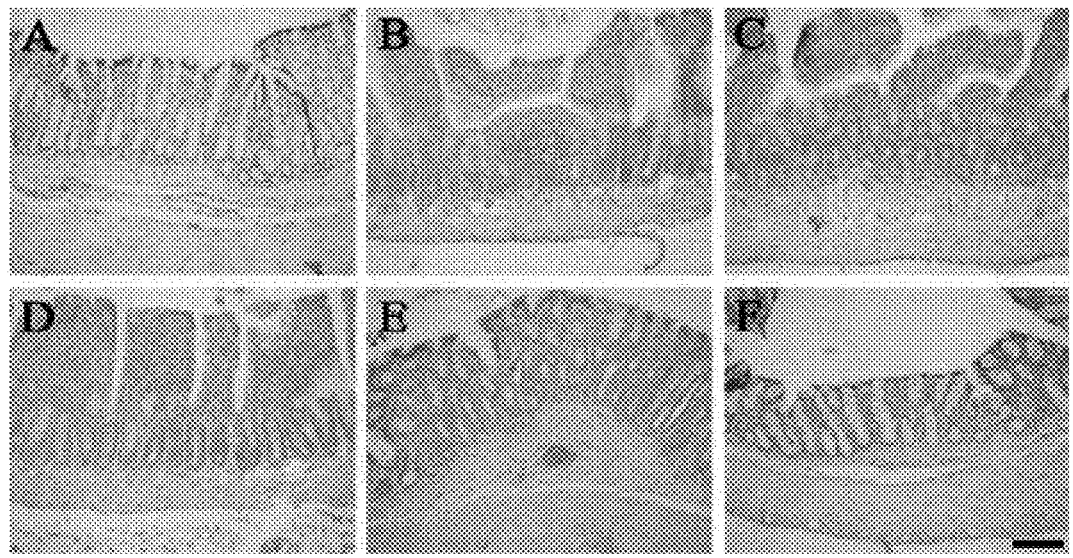
FIG. 3 shows H&E staining results of the colonic histological change due to the administration of a DNA fragment mixture in ischemic colitis-induced rats.

As shown in FIG. 3, the tissue damage including condensation and clefts in the colonic mucosa was observed in the ischemic colitis-induced group (B) compared with the normal group (A). However, the ischemia-caused condensation and clefts in colonic mucosa were observed to be reduced in the DNA fragment mixture administration groups (C, D, E, F), and the reduction was dependent on the concentration of the DNA fragment mixture administered.

Example 6-3: Masson's Trichrome Staining

In order to investigate clefts of colonic mucosa due to the administration of a DNA fragment mixture after ischemic colitis induction, the expression of the total collagen fiber was checked. Therefore, Masson's trichrome staining was conducted.

The tissue embedded in paraffin in example 6-1 was immersed in xylene to remove paraffin, hydrated, and treated with the Bouin's solution (Sigma, USA) for 1 hour. Thereafter, the tissue was washed with Weigner's iron hematoxylin solution (Sigma, USA) for 10 minutes, and washed with Biebrich scarlet-acid fuchsin solution (Sigma, USA) for 2 minutes. The washed tissue was treated with Phosphomo-lybdic-Phosphotungstic acid solution (Sigma, USA) for 10-15 minutes, treated with aniline blue solution (Sigma, USA) for 5 minutes, treated with the light green solution for 1 minute, treated with acetic solution for 5 minutes, treated with 95% ethanol and xylene, and then sealed with Permount® (Fischer Scientific, USA). The tissue stained with Masson's trichrome was observed using a microscope, and the results are shown in FIG. 4.

Figure 4:
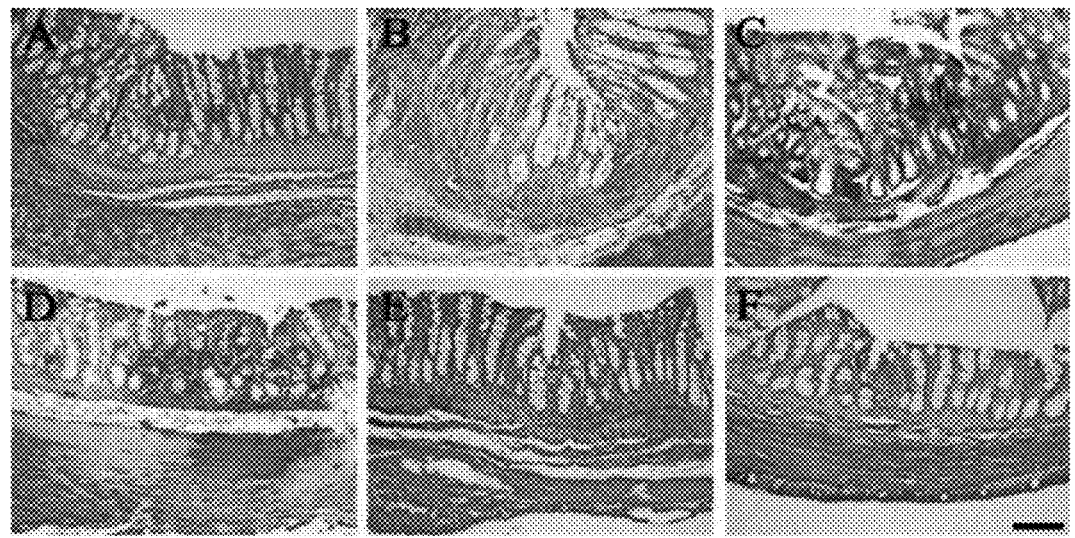
FIG. 4 shows Masson's trichrome staining results of clefts of colonic mucosa due to the administration of a DNA fragment mixture in ischemic colitis-induced rats.

As shown in FIG. 4, the clefts of colonic mucosa due to ischemia were increased in the ischemic colitis induction group (B) compared with the normal group (A), but the clefts of colonic mucosa due to ischemia were reduced in a manner dependent on the concentration of the DNA fragment mixture in the DNA fragment mixture administration groups (C, D, E, and F).

Example 7: Investigation of Protein Expression of Apoptotic Factors

The expression of apoptotic factors in association with cell necrosis due to ischemic colitis was investigated.

The colonic tissue extracted from each rat photographed for colonic tissue in example 5 was subjected to protection extraction with a lysis buffer, and the resultant product was centrifuged to obtain supernatant. Thereafter, the protein concentration was quantified using the Bio-Rad protein quantifying reagent, thereby obtaining 50 μg of proteins.

Then, 50 μg of the obtained proteins were subjected to electrophoresis using 10% SDS-PAGE, and then proteins were transferred to the nitrocellulose membrane. The protein-transferred membrane was blocked with 5% skim milk, and then treated with a primary antibody against Bax or Bcl-2 at 4° C. for 16-18 hours. Here, GAPDH antibody was used as a quantitative control. The membrane treated with the primary antibody was washed with TBST solution (Tris-buffered saline with 0.05% tween 20) three times for 10 minutes for each time. A secondary antibody against each primary antibody was added to the washed membrane, followed by reaction at room temperature for 1 hour, and the membrane was again washed with TBST solution three times for 15 minutes for each time. The washed membrane was treated with the enhanced chemiluminescence (ECL) solution to check protein bands. The results are shown in FIG. 5.

Figure 5:
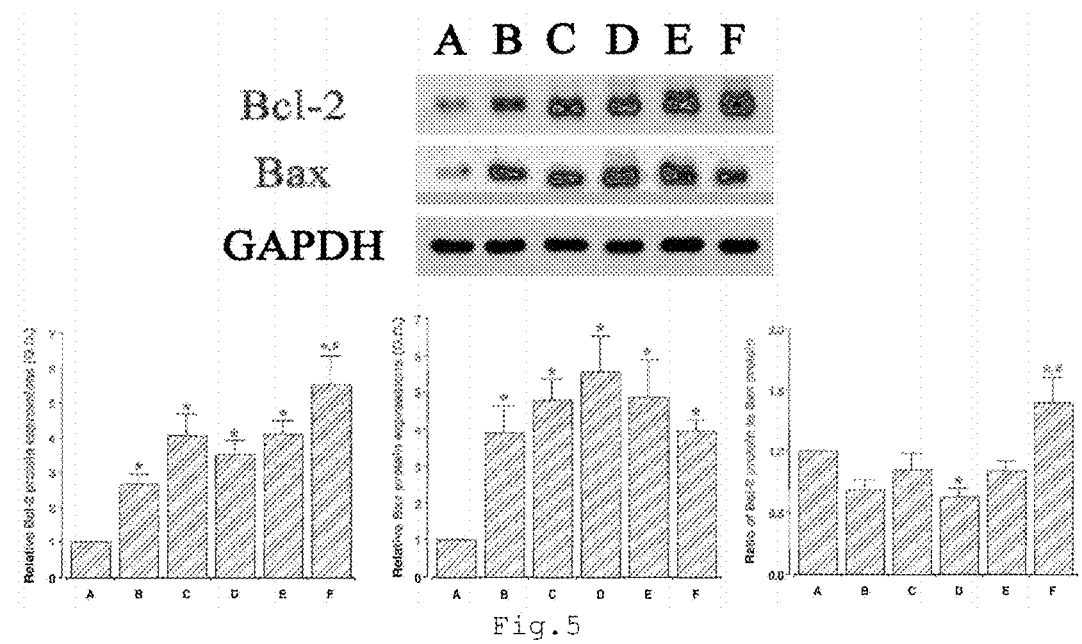
FIG. 5 shows the protein expression of apoptotic factors due to the administration of a DNA fragment mixture in ischemic colitis-induced rats.

As shown in FIG. 5, the expression of apoptotic factor Bax was increased in the ischemic colitis-induced group (B) compared with the normal group (A). The expression of Bax was increased in the DNA fragment mixture administration (2 mg/kg and 4 mg/kg) groups, but the expression of Bax was reduced in a concentration-dependent manner in the DNA fragment mixture administration (8 mg/kg and 16 mg/kg) groups. Whereas, the expression of anti-apoptotic factor Bcl-2 was increased in the DNA fragment mixture administration groups (C, D, E, F) compared with the ischemic colitis induction group (B).

It can be predicted from the above results that the DNA fragment mixture can treat ischemic colitis by inhibiting cell necrosis on the sites of occurrence of ischemic colitis.

The invention claimed is:

1. A method for treating ischemic colitis in a subject, comprising administering to the subject a therapeutically effective amount of a mixture of DNA fragments isolated from sperm or testis of fish, wherein the mixture of DNA fragments has a molecular weight of 50-1,500 kDa.

2. The method of claim 1, wherein the therapeutically effective amount is 2-25 mg/kg.

3. The method of claim 1, wherein the fish is Salmonidae fish.

4. A method for inhibiting colon cell necrosis in a subject with ischemic colitis, comprising administering to the subject a therapeutically effective amount of a mixture of DNA fragments isolated from sperm or testis of fish, wherein the mixture of DNA fragments has a molecular weight of 50-1,500 kDa.

5. The method of claim 4, wherein the therapeutically effective amount is 2-25 mg/kg.

6. The method of claim 4, wherein the fish is Salmonidae fish.

* * * * *